(12) United States Patent
Maldonado et al.

(10) Patent No.: US 8,637,727 B2
(45) Date of Patent: Jan. 28, 2014

(54) THREE-DIMENSIONAL PRINTED ARTICLE

(75) Inventors: Clarissa Maldonado, Cincinnati, OH (US); John Molander, Montgomery, OH (US); Alrick Vincent Warner, Loveland, OH (US); Thomas Alexander Horn, Hofheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 604 days.

(21) Appl. No.: 11/894,522

(22) Filed: Aug. 21, 2007

(65) Prior Publication Data

US 2008/0091162 A1 Apr. 17, 2008

Related U.S. Application Data

(63) Continuation-in-part of application No. 11/581,633, filed on Oct. 16, 2006.

(51) Int. Cl.
*A61F 13/15* (2006.01)
(52) U.S. Cl.
USPC ..................................... 604/361; 604/385.01
(58) Field of Classification Search
USPC ............................. 604/385.01, 361; 428/187
See application file for complete search history.

(56) References Cited

U.S. PATENT DOCUMENTS

| | | | | |
|---|---|---|---|---|
| 4,022,211 A | * | 5/1977 | Timmons et al. | 604/361 |
| 4,610,678 A | | 9/1986 | Weisman et al. | |
| 4,705,513 A | * | 11/1987 | Sheldon et al. | 604/361 |
| 5,260,345 A | | 11/1993 | Desmarais et al. | |
| 5,695,855 A | | 12/1997 | Yeo et al. | |
| 5,766,212 A | * | 6/1998 | Jitoe et al. | 604/361 |
| 5,899,895 A | | 5/1999 | Robles et al. | |
| 6,120,487 A | | 9/2000 | Ashton | |
| 6,297,424 B1 | * | 10/2001 | Olson et al. | 604/361 |
| 6,329,040 B1 | * | 12/2001 | Oshima et al. | 428/156 |
| 6,811,239 B1 | | 11/2004 | Salacz | |
| 7,205,041 B2 | | 4/2007 | Nair et al. | |
| 7,432,412 B2 | * | 10/2008 | Kigata et al. | 604/367 |
| 7,992,994 B2 | | 8/2011 | Kobayashi et al. | |
| 2002/0166284 A1 | | 11/2002 | Weder | |
| 2005/0219626 A1 | | 10/2005 | Moncrieff | |

FOREIGN PATENT DOCUMENTS

| | | |
|---|---|---|
| EP | 604729 B1 | 3/1998 |
| JP | 2-17947 | 2/1990 |
| JP | 5-229245 A | 9/1993 |
| JP | 7-1899 A | 1/1995 |

(Continued)

*Primary Examiner* — Lynne Anderson
(74) *Attorney, Agent, or Firm* — Andrew A Paul; Laura L. Whitmer

(57) ABSTRACT

A three dimensional printed article having a composite image printed thereon is disclosed. The composite image includes top and bottom artwork portions printed on the top and bottom surfaces of the printed article substrate. Both artwork portions are visible through a translucent or transparent substrate, thereby forming a visible composite image. The substrate can be a non-woven web. By printing on both surfaces of the substrate, the three dimensional printed article provides a good quality, aesthetically pleasing three-dimensional image that limits the loss of color and appearance of fuzz during normal use of the article. The three-dimensional printed article allows a more versatile creation of process colors and reduces the number of spot colors required to print the composite image. The three-dimensional printed article can be integrated into an absorbent article, such as a diaper. A method of printing the three-dimensional printed article and forming the absorbent article are also disclosed.

17 Claims, 3 Drawing Sheets

(56) References Cited

FOREIGN PATENT DOCUMENTS

| JP | 9-123584 A | 5/1997 |
| JP | 11-104172 A | 4/1999 |
| JP | A11-348223 | 12/1999 |
| JP | 2001-55225 A | 2/2001 |
| JP | 2001-301306 A | 10/2001 |
| JP | 2002-103900 A | 4/2002 |
| JP | 2004-50741 A | 2/2004 |
| JP | 2004-57640 A | 2/2004 |
| JP | 2004-155008 A | 6/2004 |
| JP | 2006-26081 A | 2/2006 |
| WO | WO-93/15179 A1 | 8/1993 |
| WO | WO 02/22183 A2 | 3/2002 |
| WO | WO 2004/058120 A1 | 7/2004 |
| WO | WO 2005/102237 A1 | 11/2005 |

\* cited by examiner

THREE-DIMENSIONAL PRINTED ARTICLE

CROSS-REFERENCE TO RELATED APPLICATIONS

This application is a continuation-in-part of prior co-pending U.S. application Ser. No. 11/581,633 filed on Oct. 16, 2006 which is incorporated herein by reference.

FIELD OF THE INVENTION

The present invention generally relates to printed articles for use in consumer goods such as absorbent articles and, more specifically, to a three-dimensional printed article having a three-dimensional composite image printed thereon, wherein the composite image includes image portions printed on both surfaces of the printed article.

BACKGROUND OF THE INVENTION

Absorbent articles, such as diapers and feminine hygiene products, generally include an absorbent core disposed between a liquid-permeable, body-facing topsheet and a liquid-impermeable, garment-facing backsheet. An additional layer of material is often applied to the garment-facing side of the backsheet as an external cover. The external cover can be formed from a non-woven material to provide a soft texture to the absorbent article. The external cover also can form the landing zone for a mechanical fastener, and can therefore include mechanical fastening elements, such as loops.

The external cover also can include printed images to improve the aesthetic appeal of the absorbent article. A conventional approach to providing such aesthetic appeal includes printing images on the exterior (garment-facing) surface of the external cover. This method provides good image resolution, but creates problems with color loss and fuzz visibility. Colors on the garment-facing surface of the external cover can be lost when they come into frictional contact with other surfaces, such as hands, clothes, complementary mechanical fastening elements (e.g., hooks), etc. This results both in the degradation of the printed image and the undesirable color transfer of the printed image to the contacting surface. Colors on the garment-facing surface of the external cover also increase the apparent degree of fuzz on a fibrous substrate, such as a non-woven web.

An alternate conventional approach intended to limit color loss and fuzz visibility includes printing images on the interior (body-facing) surface of the external cover. Printed in this manner, the images are only visible when viewed through the external cover, and they appear muted, having a reduced image resolution.

Accordingly, it would be desirable to provide a printed article that could be used as an external cover for an absorbent article, which printed article retains the advantages and reduces the disadvantages of the conventional printing methods. Specifically, such a printed article should advantageously exhibit good image quality, limited color loss, and a limited degree of fuzz.

SUMMARY OF THE INVENTION

Disclosed herein is a printed article generally including a translucent or transparent substrate. A portion of a composite image is printed on the top surface of the substrate and a portion of the composite image is printed on the bottom surface. The resulting printed article exhibits good image definition, low color loss and apparent fuzz, and has the unexpected benefit of providing an image with an apparent three-dimensional character. This printing scheme may be used with a wide variety of substrate-ink combinations, and may be integrated into conventional printing processes.

One aspect of the disclosure provides a printed article including a substrate having a thickness of about 60 micrometers ($\mu$m) or more, and a composite image. In another embodiment, the substrate may have a thickness of about 12 micrometers ($\mu$m) or more, and a composite image. The substrate includes a first surface and a second surface. The composite image has a composite surface area, and includes a first artwork portion having a first surface area printed on the first surface, and a second artwork portion having a second surface area printed on the second surface. The first artwork portion and the second artwork portion are visible when viewed from a vantage point above the first surface. In an embodiment, the substrate is a non-woven material. In an alternate embodiment, the substrate may be a polymeric film having a thickness of about 30 $\mu$m or more.

Another aspect of the disclosure provides an absorbent article including a topsheet having a body-facing surface and a core-facing surface, a backsheet having a garment-facing surface and a core-facing surface, and an absorbent core disposed between the core-facing surface of the topsheet and the core-facing surface of the backsheet. The absorbent article also includes a printed article substrate having a first surface and a second surface, the second surface of the printed article substrate being disposed on the garment-facing surface of the backsheet. Furthermore, the absorbent article includes a composite image having a composite surface area, the composite image including a first artwork portion having a first surface area printed on the first surface and a second artwork portion having a second surface area printed on either the second surface or the garment-facing surface of the backsheet. The first artwork portion and the second artwork portion are visible when viewed from a vantage point above the first surface.

Yet another aspect of the disclosure provides a process for forming an absorbent article, the process including the steps of (a) providing a continuous-sheet substrate having a thickness of about 60 $\mu$m or more, the substrate including a first surface and a second surface; (b) delivering the substrate to a printing apparatus including a first printing station and a second printing station; (c) printing a first artwork portion having a first surface area on the first surface; (d) printing a second artwork portion having a second surface area on the second surface; (e) cutting the continuous-sheet substrate formed by steps (a)-(d) into a plurality of printed articles; and, (f) joining each of the plurality of printed articles to an absorbent assembly. The absorbent assembly includes a topsheet having a body-facing surface and a core-facing surface, a backsheet having a garment-facing surface and a core-facing surface, and an absorbent core disposed between the core-facing surface of the topsheet and the core-facing surface of the backsheet. The first artwork portion and the second artwork portion form a composite image having a composite surface area. Furthermore, the first artwork portion and the second artwork portion are visible when viewed from a vantage point above the first surface. The printed article is joined to the absorbent assembly on the garment-facing surface of the backsheet.

Figure 1A:
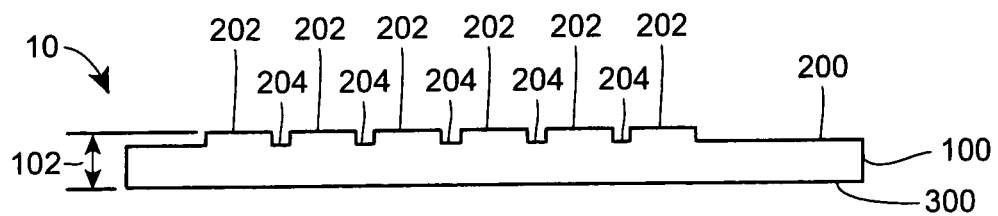
FIG. 1A is a cross-sectional view of a three-dimensional printed article.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. The drawings are not necessarily to scale.

DETAILED DESCRIPTION OF THE INVENTION

Definitions

The term "absorbent article" refers to a device that absorbs and contains liquid, and more specifically, refers to a device that is placed against or in proximity to the body of the wearer to absorb and contain the various exudates discharged from the body. Absorbent articles include items such as diapers, pull-on diapers or pant-type garments, training pants, incontinence briefs, incontinence undergarments, absorbent inserts, diaper holders and liners, feminine hygiene garments, and the like.

The term "body-facing" is used to describe a surface of an article that is in contact with or facing the body of a wearer when the article is worn. The term "garment-facing" is used to describe a surface of an article that is in contact with or facing a garment being worn when the article itself is worn.

The term "disposed" is used to mean that an element(s) is formed joined and positioned) in a particular place or position as a unitary structure with other elements or as a separate element joined to another element.

The term "joined" encompasses configurations whereby an element is directly secured to another element by affixing the element directly to the other element, and configurations whereby an element is indirectly secured to another element by affixing the element to intermediate member(s) which, in turn, are affixed to the other element.

"Mechanical fastener" refers to a fastening system or mechanism relying on physical restraint, magnetic fields, or engagement of portions of the fastener for operation. Examples of mechanical fasteners are hook-and-loop, hook-and-hook, buttons, snaps, tab-and-slot, zippers, magnet(s), and tongue-in-groove fasteners.

The terms "typical adhesive" and "traditional adhesive" are interchangeable and refer to an adherent which demonstrates adhesion when applied to another material generally (i.e., the other material is not specially selected). Traditional adhesive materials connect to other materials indiscriminately and may stick to a variety of materials.

The terms "stretchable" or "elastic" refer to materials which are extensible and which also return to substantially their original dimensions when the external pulling force is removed. The term "extensible" refers to materials which elongate or increase in at least one dimension when subject to an external pulling force.

"Color concentration" refers to the fractional surface area of a printed region that is actually printed with ink. A color concentration of less than 1.0 can be used to provide a lighter apparent region color (e.g., when the underlying substrate is white or clear). A visual blend (or "build") of two overlaying colors resulting in a third, different apparent composite color is also possible when the color concentration of the top overlaying color is less than 1.0. Typical color concentrations that are useful when building composite colors include, for example, less than about 0.75, less than about 0.5, and less than about 0.25, less than about 0.10, and less than about 0.05.

"Color density" refers to the fraction of incident light reflected from a surface. The color density of a printed surface is unitless and is determined as $\log_{10}(1/R)$, where R is the fractional reflectance of incident light from the surface. For example, a printed surface that reflects 10% of incident light has a fractional reflectance R=0.1 and a color density of 1.0 (i.e., $\log_{10}(1/0.1)$). Color density and/or reflectance can be measured with a color meter (available, for example, from GretagMacbeth, LLC, New Windsor, N.Y.).

"Visible" refers to an image or color as it appears when viewed from a particular vantage point, and may be the image or color that results from the superposition of two overlaying images or colors. Unless specified otherwise, the vantage point from which a printed article substrate is viewed is a point displaced above the first (or garment-facing) surface of the substrate, such that the normal distance from the vantage point to the first surface of the substrate is less than the normal distance from the vantage point to the second (or body-facing) surface of the substrate.

The term "spot color" refers to a color applied directly to a substrate by a printing apparatus with a single ink color. A spot color need not be a primary color. It can represent a single blend of multiple ink colors, which blend is applied to the substrate as a single color in a single application step. In contrast, a "process color" is a color that is formed by the application of two or more color inks to the same region of a substrate to form an apparent third color (e.g., application of yellow and red colors to build orange). A process color can be formed with a layered application of two (or more) color inks on the same surface of the substrate. Within the context of the present disclosure, a process color can also be formed by applying at least one color ink on each of two opposing, vertically aligned surfaces of the substrate.

Three-Dimensional Printed Article

Figure 1B:
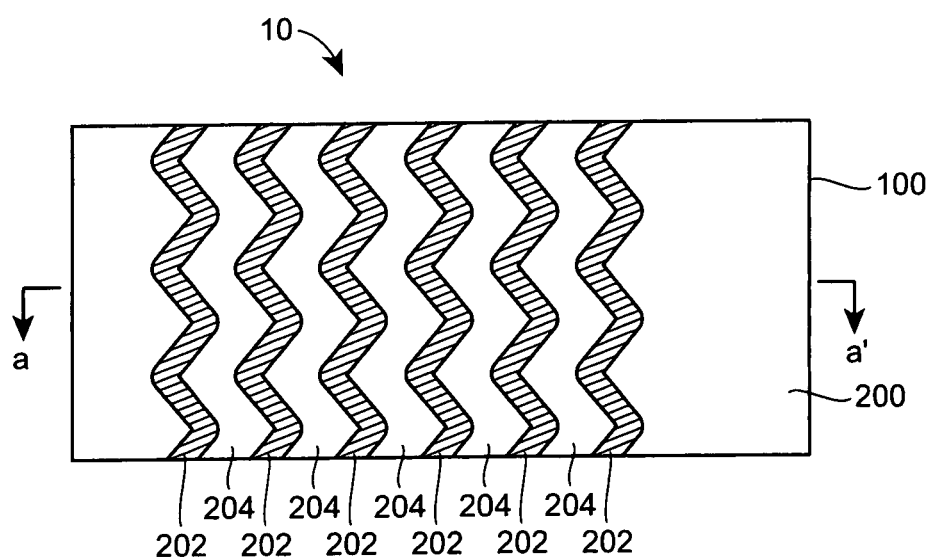
FIG. 1B is a top plan view of the three-dimensional printed article of FIG. 1A.

FIGS. 1A and 1B illustrate a substrate used in a three-dimensional printed (3DP) article according to the present disclosure.

FIGS. 1A and 1B show a substrate 100 of a 3DP article 10. FIG. 1A is a cross-sectional view of the 3DP article 10 taken along line a-a' shown in FIG. 1B. The substrate 100 is generally planar, and has a first surface 200 and a second surface 300 opposing the first surface 200. When integrated into an absorbent article (e.g., a diaper), the first surface 200 is generally on the garment-facing side of the absorbent article, and the second surface 300 is generally on the body-facing side of the absorbent article. Thus, any images on the 3DP article 10 should be visible when viewed from the above the first surface 200, for example from a vantage point V as shown in FIG. 1A.

In FIG. 1A, the second surface 300 is illustrated as a generally planar, smooth surface, while the first surface 200 is illustrated as a generally non-planar, contoured surface. The first surface 200 includes a series of ridges 202 disposed thereon that define a series of recessions 204 between the ridges 202. The non-planar contour of the first surface 200 can be an intentional design selection for any arbitrary substrate material, which design selection is intended to enhance the three-dimensional appearance of an image printed on the 3DP article 10 or to provide an aesthetic pattern (e.g., a quilted surface) on the substrate 100 absent a printed image. In the case of a non-woven substrate 100, the recessions 204 can represent bonding sites for the non-woven material. The second surface 300 is generally selected to be smooth to facilitate attachment of the 3DP article 10 to another structure in a composite article, for example the backsheet of an absorbent article. In more general embodiments (not shown), either, neither, or both of the first surface 200 and second surface 300 can be generally smooth or contoured.

The substrate 100 has a thickness 102 that is generally the normal distance between the first surface 200 and the second surface 300, as shown in FIG. 1A. The thickness 102 includes the contribution of any non-planar elements of the substrate 100, such that the thickness 102 represents the maximum normal distance between two points on the first surface 200 and the second surface 300. For example, as shown in FIG. 1A, the thickness 102 includes a contribution from the ridges 202 as well as a contribution from the bulk portion of the substrate 100.

The substrate 100 is generally a translucent material, but also can be transparent. In one embodiment, the substrate 100 itself is not colored; the only color comes from images printed onto the substrate 100. Thus, substrate 100 would generally be white when made from a translucent material, and would generally be colorless and clear when made from a transparent material. However, in an alternate embodiment, the substrate 100 may be itself tinted with a colorant, but only to the extent that the substrate 100 retains its translucent or transparent character.

Figure 2A:
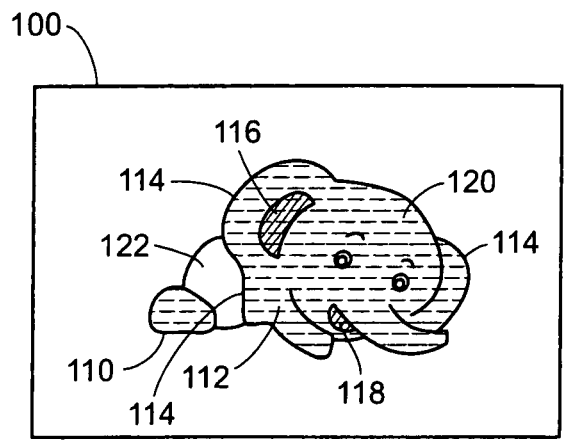
FIG. 2A is a top plan view of a composite image on the three-dimensional printed article of FIG. 1A.
Figure 2B:
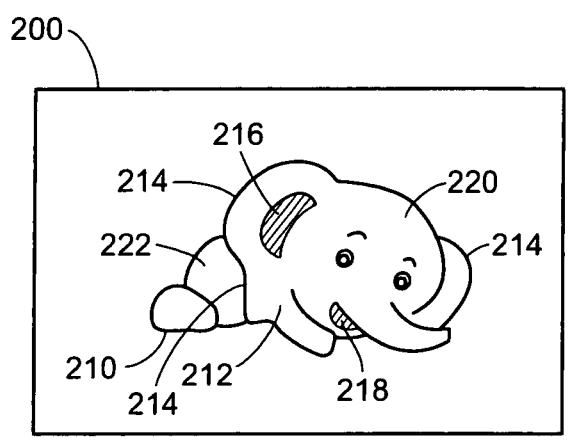
FIG. 2B is a top plan view of a first artwork portion on the three-dimensional printed article of FIG. 1A.
Figure 2C:
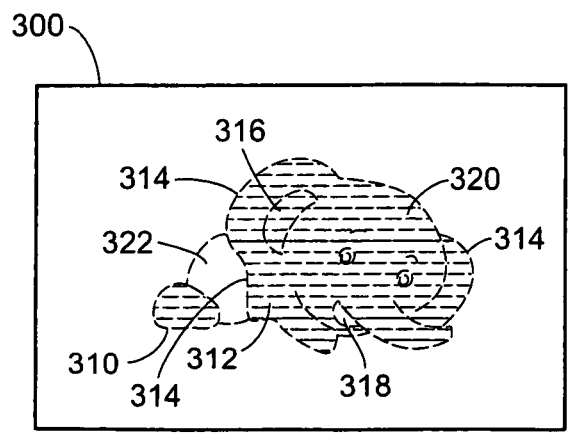
FIG. 2C is a top plan view of a second artwork portion on the three-dimensional printed article of FIG. 1A.

FIGS. 2A to 2C illustrate the manner in which a three-dimensional composite image is formed using multiple artwork portions disposed on different locations of the substrate 100.

FIG. 2A shows a composite image 110 that is the visible superposition of a first artwork portion 210 (shown in FIG. 2B) and a second artwork portion 310 (shown in FIG. 2C). Because of the translucent/transparent character of the substrate 100, both the first artwork portion 210 and the second artwork portion 310 (and, thus, the composite image 110) are visible when viewed from above the first surface 200. The composite image 110 illustrated in FIG. 2A is a cartoon character; however, the composite image 110 can generally include any kind of image such as, for example, a non-cartoon picture, a colorful pattern of shapes, and/or words/logos.

The composite image 110 includes several image elements. A composite outline element 114 is generally a thin, dark element used to define the outer boundaries of the composite image 110 and to provide contrast between different interior regions of the composite image 110. A build color region 116 is a colored region whose visible color is based on a combination of two different colors applied to the first surface 200 and the second surface 300. An overcolor region 118 is a colored region whose visible color is based on a color applied to the first surface 200. Similarly, an undercolor region 120 is a colored region whose visible color is based on a color applied to the second surface 300. A void color region 122 is a region with no applied color, having only the color of the underlying substrate 100 (which may include a tint). The composite outline element 114 may be black, the build color region 116 may be grayish red, the overcolor region 118 may be red, and the undercolor region 120 may be gray. However, these colors are only illustrative, and any selection of colors is possible.

FIG. 2B shows the first artwork portion 210 of the composite image 110. The first artwork portion 210 is printed on the first surface 200 of the substrate 100. Generally, elements of the first artwork portion 210 include those areas or regions where it is desirable to provide definition and/or vibrant colors to the resulting composite image 110, because the visibility of these elements is not blurred and/or partially obscured by the intervening substrate 100 when viewed from above the first surface 200. In the embodiment illustrated in FIG. 2B, the first outline element 214 is a thin, dark element (e.g., a black line) used generally to define the outer boundaries and interior features of the composite image 110. A first build color region 216 is a colored region (e.g., colored red) with a color concentration less than 1. A first overcolor region 218 is also a colored region (e.g., colored red), generally with a color concentration of about 1, although lower color concentrations can be used for lighter image colors. A first undercolor region 220 and a first void color region 222 have no applied color.

FIG. 2C shows the second artwork portion 310 of the composite image 110. The second artwork portion 310 is printed on the second surface 300 of the substrate 100. Generally, colored elements of the second artwork portion 310 include those areas or regions where it is desirable to minimize image deterioration, because the second surface 300 is typically the body-facing surface and, when integrated into a composite absorbent article structure, is less subject to image-destructive events. In the embodiment illustrated in FIG. 2C, a second build color region 316 and a second undercolor region 320 are colored (e.g., colored gray), generally with a color concentration of about 1, although lower color concentrations can be used for lighter image colors. This results in a visible color (e.g., grayish red) for the build color region 116 that is a mixture of the colors of the first and second build color regions 216 and 316, respectively (because, for example, a partial red color is overlaid on an underlying gray color), and results in an unmixed visible color for the undercolor region 120 (because there is no other color in the first undercolor region 220 atop the second undercolor region 320). A second overcolor region 318 and a second void color region 322 have no applied color.

The first artwork portion 210 and the second artwork portion 310 can be at least partially vertically aligned, and are generally vertically aligned such that the colored regions on a surface are coincident with complementary regions defined by outline elements on an opposing surface. Dashed lines 314 of FIG. 2C are provided to indicate the alignment of the first artwork portion 210 and the second artwork portion 310 when superimposed, and the dashed lines 314 are not actually printed on the second surface 300.

However, in some embodiments, the dashed lines of FIG. 2C indicate the location of a second outline element 314 that is printed on the second surface 300. This duplicate printing of both the first outline element 214 and the second outline element 314 can be desirable when image deterioration on the first surface 200 is expected during normal use of the 3DP article 10; in such cases, the second outline element 314 provides definition for the composite image 110 in areas where the first outline element 214 may have deteriorated.

The composite image 110 has a composite surface area 112. The composite surface area 112 includes the visible printed image area of the composite image 110, regardless of whether printed on the first surface 200, the second surface 300, or both. For example, the composite surface area 112 shown in FIG. 2A includes the printed surface area of the outline element 114 and the colored regions 116, 118, and 120, but excludes the surface area of void color region 122. Similarly, the first artwork portion 210 has a first surface area 212 and the second artwork portion 310 has a second surface area 312. These surface areas represent the actual printed areas on the first and second surfaces 200 and 300, respectively. For example, the first surface area 212, shown in FIG. 2B, includes the printed surface area of the first outline element 214, the first build color region 216, and the first overcolor region 218. Similarly, the second surface area 312, shown in FIG. 2C, includes the printed surface area of the second build color region 316 and the second undercolor region 320.

It is often desirable to select the various printed areas so that the majority of the printed area is on the second surface 300. This is the case when some deterioration of the composite image 110 is expected, for example due a loss of ink from the substrate 100 or due to physical destruction of a portion of the substrate 100. Such image deterioration is most likely on the first surface 200 (which is typically the garment-facing surface in an absorbent article) when abrasion between the first surface 200 and, for example, a garment (i.e., of the absorbent article wearer) or the floor (e.g., when the absorbent article is a diaper worn by a baby) can result in a loss of printing ink. Similarly, a portion of the first surface 200 may be the landing zone for mechanical fastening elements or an adhesive strip; this portion of the first surface 200 can be subject to substantial destruction resulting from subsequent fastening and defastening events in the landing zone. To limit the impact of such deterioration, the ratio of first surface area 212 to the composite surface area 112 is generally about 0.5 or less, about 0.2 or less, or about 0.1 or less, for example about 0.05 or less. With these ratios, more of the composite image 110 will remain intact during the useful life of the 3DP article 10 (or an absorbent article of which it is a part).

Another way to mitigate the effect of image deterioration is to overprint certain regions of the composite image 110. In such an embodiment, the overcolor region 118, the undercolor region 120, and/or portions thereof can have colors applied to both the first surface 200 and the second surface 300. However, the applied colors are the same on both surfaces. This overprinting of the same color is useful in regions of the composite image 110 where some degree of image deterioration is expected because image loss on the first surface 200 reveals the identical underlying image portion on the second surface 300. When a portion of the composite image 110 is overprinted with duplicate, overlaid images, the ratio of the sum of the first surface area 212 and the second surface area 312 to the composite surface area 112 is greater than 1.0 and is 2.0 or less. When overprinted, this ratio is generally in a range of about 1.2 to 2.0, for example about 1.5 to 2.0, and can be 2.0 when identical images are printed on the first and second surfaces 200, 300.

However, it may also be desirable to increase the fraction of the printed area that is on the first surface 200. Because of the thickness 102 of the substrate 100, the contrast between images printed on the first surface 200 and those printed on the second surface 300 can create an aesthetically pleasing three-dimensional relief effect. For example, in an alternate embodiment (not shown), the entire cartoon character illustrated by the composite image 110 is printed on the first surface 200, and a background color/pattern (not shown) is printed on a visible portion of the second surface 300. This provides a visible three-dimensional effect in which the cartoon character is displaced away from the background and therefore appears in the foreground of the image.

The 3DP article 10 also provides a convenient means to blend two different colors in a printing process (in which the number of available printing colors might be limited) to build a visible composite color that is different from the two printed colors. As illustrated in FIGS. 2A to 2C, the build color region 116 includes the first build color region 216 disposed on the first surface 200 that is at least partially vertically aligned (or even completely vertically aligned) with the second build color region 316 disposed on the second surface 300. The first build color region 216 is printed with a first color and the second build color region 316 is printed with a second color. The first color is printed with a color concentration less than 1.0 so that both the first and second colors are visible and, therefore, blend to form the composite color when viewed from above the first surface 200.

In general, the top and bottom colors can each either be spot colors or themselves build colors. For instance, in the illustrated embodiment, first build color region 216 may be red and the second build color region 316 may be gray, and these colors can be obtained by printing with a red spot color as the first color and by printing with a gray spot color as the second color. Alternatively, the first color could be a purple build color formed with a red spot color and a blue spot color. Thus, the final visible composite color in the build color region 116 would be grayish purple.

This manner of forming build colors in the composite image 110 is advantageous because it results in images having a greater resiliency to wear. Typical printing inks adhere more strongly to the substrate 100 than they do to each other. When the first and second colors are printed on the substrate 100 in the first and second build color regions 216 and 316, respectively, the inks are less likely to be removed during the course of normal use of the 3DP article 10. When, for example, the first color is printed directly on the substrate 100 and the second color is printed on the first color, the second color can more easily be lost during normal use of the 3DP article 10, causing a potentially undesirable discoloration.

Forming build colors in the composite image 110 by printing on the first and second build color regions 216 and 316 can also improve the print vibrancy of the 3DP article 10. Specifically, the build color region 116 generally has a color density increase of at least about 0.1 when measured from above the first surface 200. The color density increase is the color density of the build color region 116 relative to the color density of a printed article in which the first and second colors of the first and second build color regions are printed on the first surface. The color density increase can also be at least about 0.2, for example at least about 0.3.

From the foregoing, it is apparent that the various embodiments provide a versatile means to tailor a 3DP article to a variety of applications in a way that combines desirable aesthetic image qualities with an increase in image durability when subjected to normal wear during use.

Three-Dimensional Printed Article Fabrication

The substrate to be printed with an ink composition generally includes materials such as a non-woven web, a woven fabric, a polymeric film, combinations thereof, and laminates thereof. A non-woven web is suitable for a 3DP article intended for use in an absorbent article to provide a cloth-like feeling and an aesthetically appealing appearance. The thickness of the substrate is generally about 60 μm or more and about 400 μm or less. Alternatively, the thickness of the substrate is about 12 μm or more, about 15 μm or more, about 18 μm or more. When the substrate is a fibrous material (e.g., a non-woven web, a woven fabric), the thickness can be in a range of about 80 µm to about 200 µm, for example about 100 µm to about 200 µm. Alternatively, when the substrate is a fibrous material, the thickness can be about 12 µm or more, about 15 µm or more, about 18 µm or more. When the substrate is a polymeric film material, the thickness can be at least about 30 µm or more, for example in a range of about 50 µm to about 200 µm, but is generally in a range of about 80 µm to about 200 µm, for example about 100 µm to about 200 µm.

The non-woven web and the woven fabric can include natural fibers, synthetic fibers, or a combination of natural and/or synthetic fibers. Suitable natural fibers include wood, cotton, wool, silk, hair, burlap, linen, cellulosic fibers, and combinations thereof. Suitable synthetic fibers include polyolefins (e.g., low density polyethylene, linear low density polyethylene, high density polyethylene, polypropylene), polyamides, polyester, nylon, rayon, and combinations thereof. In woven fabrics, these polymers can be made into continuous fibers which are, in turn, woven into a fabric. In non-woven webs, the synthetic fibers may be long, generally continuous fibers such as spunbond and meltblown fibers, or they may be shorter staple-length fibers, such as are commonly used in carded webs. The fibers may have any shape, such as a circular cross section shape or a non-circular cross section shape. The resulting non-woven web or woven fabric can be multi-layered, be stretchable, and/or include a mechanical fastening element. The basis weight for the non-woven web or woven fabric is generally in a range of about 10 grams per square meter ($g/m^2$) to about 100 $g/m^2$, for example about 30 $g/m^2$ to about 70 $g/m^2$.

In many embodiments, a polyolefin non-woven web is used for reasons such as cost, processability into the form of fibers, and/or softness in the form of fibers. A suitable non-woven web for use in the 3DP article is available from Mitsui Chemical (Japan) under the product code NWLZ-060111-2. This non-woven web is a polypropylene spunbond with female mechanical fastening elements disposed on its surface, has a basis weight of about 45 $g/m^2$, and has a thickness of about 100 µm (when measured from its base to the furthest extent of its mechanical fastening elements).

The polymeric film can be liquid impermeable, liquid permeable, vapor permeable, vapor impermeable, stretchable, multi-layered, or a laminate (e.g., with a non-woven web). Suitable polymers for the film include polyolefins such as low density polyethylene, linear low density polyethylene, high density polyethylene, polypropylene, and combinations thereof. Such polyolefin-based polymers may be extruded, cast or blown into films for subsequent use according to the present invention. The basis weight for the polymeric film is generally in a range of about 10 $g/m^2$ to about 50 $g/m^2$.

A wide variety of ink formulations can be used when printing the 3DP article. Both water- and solvent-based inks can be used with non-woven webs, woven fabrics, and polymeric films. Either or both of pigments and dyes can be used as colorants. Pigments are generally used as colorants because they have an increased resistance to water, reducing the possibility of color loss when the 3DP article is integrated, for example, into an absorbent article. A corona discharge treatment can be performed on the substrate to improve transfer and adhesion of the ink colorant to the substrate (in particular a polyolefin substrate). Adhesion to the substrate can also be improved by using ultraviolet-curing inks, electron beam-curing inks, and/or an adhesive additive such as polyvinyl alcohol or ethylene vinyl acetate. Novelty inks such as disappearing inks and other additives such as detergents, foams, surfactants, and abrasives can also be used. Suitable sources of printing inks include Environmental Inks and Coatings (Morganton, N.C.) and Inx International Ink Co. (Schaumburg, Ill.).

Conventional printing methods and equipment such as rotogravure, flexographic, screen printing, and ink jet printing are suitable for printing the 3DP article. The ink can be applied directly to the substrate (e.g., ink jet printing) or the ink can be applied first to a transfer surface such as a printing roll and then to the substrate from the transfer surface (e.g., rotogravure, flexographic, or screen printing). Rotogravure printing uses an engraved print roll and provides high quality, high speed, single-color prints. Screen printing is suitable for water-based and hot-melt inks, but it is generally not as fast as, for example, flexographic printing. Ink jet printing is suitable for low-viscosity inks and can be performed at high speeds.

In many embodiments, flexographic printing is used because of the suitability of the method in printing soft substrates, the speed of production, and cost factors. The flexographic printing process uses a raised printing surface made of a flexible material to transfer an ink image to the substrate. The flexible surface can transfer a good image even to a rough substrate surface. The printing can accommodate multiple colors. Flexographic printing equipment is versatile because it is relatively easy to change print graphics and the printing plates are less expensive than some of the other equipment types. Suitable liquid inks can be solvent- or water-based, and they dry mainly by evaporation. A wide variety of anilox roll densities and volumes can be used, with suitable printing equipment using, for example, 360 lines per inch (lpi), 480 lpi, or 600 lpi anilox rolls. A suitable printing press is a 12-station UV-flexographic press available under model number FB 2500 from Nilpeter USA (Cincinnati, Ohio).

In a process for printing the 3DP article, the substrate is generally provided in the form of a continuous sheet. The substrate can have any of the properties described above (e.g., material composition, thickness, basis weight). In an embodiment, the substrate is continuously delivered to a printing apparatus having a first printing station and a second printing station. The first and second printing stations are used to print the first and second artwork portions (as described above) on the first and second surfaces of the substrate, respectively. As described above, the first and second artwork portions form a composite image, and both are visible when viewed from above the first surface of the substrate. Once the continuous-sheet substrate is printed with the first and second artwork portions, it is typically cut into a plurality of individual 3DP articles that can be integrated into an individual absorbent article.

The first and second printing stations refer to the portions of the printing apparatus allowing it to print on both sides of the substrate. A typical printing apparatus is capable of printing on only one surface of the substrate at a time. In this case, the first and second printing stations are physically located in discrete portions of the printing apparatus (e.g., at different linear distances along the length of the printing apparatus). The continuous-sheet substrate initially enters the first print station where ink is applied to the first substrate surface. While inside the printing apparatus, the continuous-sheet substrate is rotated (e.g., with a turn bar) such that the second substrate surface faces the printing mechanism of the printing apparatus. Then, the continuous-sheet substrate enters the second print station where ink is applied to the second substrate surface. Alternatively, the first and second printing stations can be physically located in the same portion of the printing apparatus (i.e., at the same linear distance along the length of the printing apparatus). In this case, ink is applied to both sides of the substrate simultaneously.

In an alternate embodiment, the first and second print stations can be the same physical print station in a single printing apparatus. In this case, the continuous sheet substrate is registered and fed to the printing apparatus to print the first artwork portion on the first surface of the substrate. Then, the substrate is flipped and re-fed to the printing apparatus to print the second artwork portion on the second surface of the substrate, using the registration mark to ensure that the first and second artwork portions are properly aligned.

The first and second printing stations can be used to apply different colors in overlapping regions on the first and second surfaces of the substrate to form a build color region as described above. An advantage of forming build color regions in this manner is that the number of colors can be reduced, thereby increasing process efficiency. The first and second printing stations (and, therefore, the first and second artwork portions) each include at least one spot color. The sum of the number of spot colors distributed among the first and second printing stations (or, equivalently, the first and second artwork portions) is generally not more than about 8, not more than about 6, for example not more than about 4.

Application—Absorbant Article

Figure 3:
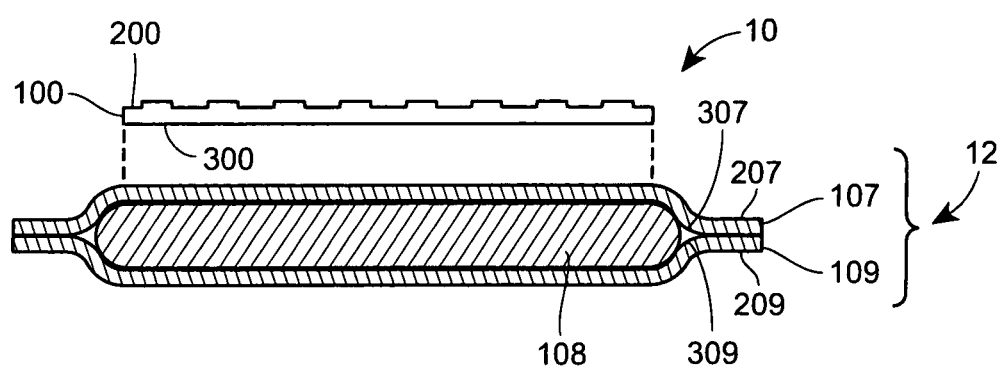
FIG. 3 is a side view of an absorbent assembly including the three-dimensional printed article of FIG. 1A.

FIG. 3 illustrates the use of a 3DP article integrated as a component of a consumer good such as an absorbent article. Suitable absorbent articles include diapers (e.g., pants-type, taped), adult incontinence products, feminine hygiene products, and the like. The absorbent article shown in FIG. 3 includes an absorbent assembly 12 that may constitute the main structure of the absorbent article with other features added to form the composite absorbent article structure. For example, a pants-type diaper would include additional structure to form a waistband and a taped diaper would include ears with a fastening means (e.g., mechanical fastener, conventional adhesive, etc.) disposed thereon.

The absorbent assembly 12 includes a liquid pervious topsheet 109, a backsheet 107, and an absorbent core 108, and has the 3DP article 10 integrated therein. Alternatively, the 3DP may be printed directly on the backsheet 107 and/or directly on the topsheet 109. The topsheet 109, the backsheet 107, and the absorbent core 108 may be assembled in a variety of configurations well known in the art. Representative absorbent assembly structures are described in U.S. Pat. Nos. 5,899,895 and 6,120,487.

The backsheet 107 is generally that portion of the absorbent assembly 12 which is disposed adjacent the absorbent core 108 and which prevents the excreta and/or exudates contained therein from soiling garments or other articles possibly contacting the absorbent article, such as bedsheets and clothing. The backsheet 107 has a garment-facing surface 207 and a core-facing surface 307. In many embodiments, the backsheet 107 may be substantially impervious to liquid and may include any suitable thin plastic film known in the art, including a breathable film. Suitable backsheet films include those manufactured by Tredegar Industries, Inc. (Terre Haute, Ind.), and sold under the trade names X15306, X10962, and X10964.

In the illustrated embodiment, the topsheet 109 is disposed adjacent the absorbent core 108 and may be joined to the absorbent core 108 and/or to the backsheet 107 by any attachment means known in the art, for example as discussed in the '895 and '497 patents mentioned above. The topsheet 109 has a body-facing surface 209 and a core-facing surface 309. The topsheet 109 is generally compliant, soft-feeling, and non-irritating to the wearer's skin. At least a portion of the topsheet 109 can be liquid pervious, permitting liquids to readily penetrate through its thickness. A suitable topsheet may be manufactured from a wide range of materials known in the art, such as porous foams, reticulated foams, apertured plastic films, or woven or nonwoven materials of natural fibers such as wood or cotton fibers, or synthetic fibers such as polyester or polypropylene fibers, or a combination of natural and synthetic fibers. If the topsheet 109 includes fibers, the fibers may be spunbond, carded, wet-laid, meltblown, hydroentangled, or otherwise processed as is known in the art. One suitable topsheet material is a thermobonded carded web which is available as Supplier Code No. P-8 from Fiberweb North America, Inc. (Simpsonville, S.C.).

The absorbent core 108 is disposed between the topsheet 109 and the backsheet 107, and is adjacent the core-facing surfaces 307 and 309. The absorbent core 108 may include any absorbent material which is generally compressible, conformable, non-irritating to the wearer's skin, and capable of absorbing and retaining liquids such as urine and other bodily exudates. The absorbent core 108 may be manufactured in a wide variety of sizes and shapes, for example, rectangular, hourglass, "T"-shaped, asymmetric, etc. The absorbent core 108 may include any of a wide variety of liquid-absorbent materials commonly used in disposable diapers and other absorbent articles, such as comminuted wood pulp, which is generally referred to as airfelt, cellulose wadding, meltblown polymers, chemically stiffened, modified, or cross-linked cellulosic fibers, tissue, absorbent foams including those prepared from polymerization of a high internal phase emulsion, superabsorbent polymers, absorbent gelling materials, or any other known absorbent material or combinations of materials. Suitable absorbent core structures are described in U.S. Pat. Nos. 4,610,678 and 5,260,345.

The 3DP article 10 is integrated into the absorbent assembly 12 by attaching the second surface 300 of the substrate 100 to the garment-facing surface 207 of the backsheet 107. The 3DP article 10 can have any combination of the features described above when included in the absorbent assembly 12. In an alternate embodiment (not shown), the absorbent assembly 12 can have the same composite structure shown in FIG. 3, with the difference being that the second artwork portion 310 (and all of its attendant components) is printed on the garment-facing surface 207 of the backsheet 107 instead of the second surface 300 of the substrate 100. In this case, the resulting composite image 110 is the same as described above. This alternate embodiment takes advantage of the fact that a printing process step is generally performed for the backsheet 107 regardless of whether the 3DP article 10 is integrated into the absorbent assembly 12; therefore, printing the second artwork portion 310 on the backsheet 107 reduces the complexity of the printing process for the substrate 100. Alternatively, the 3DP may be printed directly on the backsheet 107 and/or directly on the topsheet 109.

The 3DP article 10, the backsheet 107, the absorbent core 108, the topsheet 109, can be joined to each other or any other element of the absorbent article by any attachment means known in the art. For example, the attachment means may include a uniform continuous layer of adhesive, a patterned layer of adhesive, or an array of separate lines, spirals, or spots of adhesive. Suitable adhesives include those manufactured by H.B. Fuller Company (St. Paul, Minn.) and marketed as HL-1620 and HL-1358-XZP. Alternately, the attachment means may include heat bonds, pressure bonds, ultrasonic bonds, dynamic mechanical bonds, or any other suitable attachment means or combinations of attachment means known in the art.

EXAMPLES

For each of Examples 1-3, a composite image is printed onto a continuous polyolefin non-woven web substrate. The non-woven web substrate is a polypropylene spunbond (45 g/m$^2$ basis weight, about 100 μm thickness, available from Mitsui Chemical (Japan)) that is a whitish translucent material. The top (or first) surface of the substrate is contoured, having a soft fabric texture, and includes the loop elements of a mechanical fastener thereon. The bottom (or second) surface of the substrate is smooth.

The composite image printed on the substrate includes a cartoon character, similar to the one shown in FIGS. 2A through 2C, and a background. The cartoon character has a red body, an orange nose, and dark blue outline elements. The background generally has a colorful pattern and a word logo as its features, and these features include the colors yellow, magenta, cyan, and green. The composite image has an approximate surface area (including the cartoon character and the background) of 50 cm$^2$ (about 11.4 cm×4.4 cm) and the cartoon character alone has an approximate surface area of 8 cm$^2$ (about 2.5 cm×3.2 cm).

The composite image is printed with a Nilpeter FB-2500 printing press (using 480 lpi anilox rolls and operating at a speed of about 1 m/s; available from Nilpeter USA, (Cincinnati, Ohio)). Six color inks are used: cyan, magenta, yellow, PMS032 red, PMS2745 blue, and PMS3272 green (available from Environmental Inks and Coatings (Morganton, N.C.)). An orange build color is formed by combining red and yellow.

After printing, the composite image is generally inspected for print quality. Additionally, a tab containing the hook elements of a mechanical fastener is affixed to the top surface of the substrate and then removed. This defastening event damages a portion of the substrate, creating a top surface portion that is relatively fuzzy (i.e., compared to the substrate in its initial state). After the defastening event, the substrate is inspected for image loss and substrate deterioration. The composite image and substrate are viewed from above the top surface of the substrate when they are inspected.

Specific details for the printing process and the inspection evaluation are set forth below for each example.

In Example 1, all features of the composite image are formed by printing onto the top surface of the substrate. The colors are bright, there is sharp definition between the various features, and the word logo is legible. The composite image, with the cartoon character and the background both on the top surface, has a two-dimensional appearance. After the defastening event, the composite image exhibits locations where color loss is substantial. The colors that remain on the substrate after the defastening event accentuate the surface damage caused thereby, making the resulting fuzz more apparent.

In Example 2, all features of the composite image are formed by printing onto the bottom surface of the substrate. The colors and features appear muted behind the translucent substrate, and the word logo is only legible upon close inspection. The composite image, with the cartoon character and the background both on the bottom surface, has a two-dimensional appearance. After the defastening event, the composite image exhibits no color loss, and the generation of fuzz is only apparent upon close inspection.

In Example 3, the body and outline elements of the cartoon character are printed on the top surface of the substrate. The background patterns and logo are printed on the bottom surface of the substrate. The orange nose of the cartoon character is built by printing a red nose on the top surface of the substrate and by printing a yellow nose on the bottom surface of the substrate. The composite image is printed on the substrate in one printing event (i.e., in a single printing press) in which (1) two spot colors (red and blue) are printed on the top surface of the substrate in a first print station, (2) a TEFLON-coated turn bar inserted into the print line rotates the continuous substrate 180° as it travels from the first to second print stations, and (3) four colors (cyan, magenta, yellow, and green) are printed on the bottom surface of the substrate in a second print station. In the resulting 3DP article, the ratio of the cartoon character surface area (i.e., that portion on the top surface) to the composite image surface area is about 0.16.

In the resulting 3DP article of Example 3, the colors of the cartoon character are bright, and the outline elements provide sharp definition of its features. The background colors are muted behind the translucent substrate, and the resulting contrast between the cartoon character and background creates a three-dimensional effect in which the cartoon character appears to be in the image foreground. The word logo in the background is only legible upon close inspection. The defastening event is applied to a local region of the composite image where there are some outline elements on the top surface of the substrate, but the majority of the region's surface area includes background features printed on the bottom surface. While some color loss is evident from the outline elements, the low relative surface area of the outline elements results in minimal image loss and minimal apparent fuzz.

The creation of the orange build color in Example 3 illustrates the process efficiency benefit of forming a build color region in a 3DP article by printing on opposing surfaces of the substrate. Each of Examples 1-3 uses six colors. If the orange nose of the cartoon character were built by printing on both the top and bottom surfaces of the substrate, a total of seven colors would be required for Example 3. For example, the orange nose could be printed with the addition of an orange spot color in the first print station, for a total of three colors in the first portion of the press (i.e., red, blue, and orange) and a total of seven process colors in the complete printing process (i.e., adding cyan, magenta, yellow, and green in the second print station). Alternatively, the orange nose could be built with red and yellow spot colors both applied to the top surface of the substrate in the first part of the press. However, this still would require an additional process color (i.e., red, blue, and yellow in the first part of the press; cyan, magenta, yellow, and green in the second part of the press).

The creation of the orange build color in Example 3 also illustrates the increased print vibrancy of a 3DP article. When measured with a GretagMacbeth color meter (New Windsor, N.Y.) from above the top surface of the substrate, the orange nose of the cartoon character from Example 1 has a color density of 0.1. The orange nose of the cartoon character from Example 3 similarly measured has a color density of 0.41, thus exhibiting a color density increase of 0.31.

These examples illustrate the ability of a 3DP article to provide pleasing aesthetic features with an increased image resiliency while maintaining process efficiency.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and the scope of the invention. It is therefore intended to cover in the appended claims all such changes and modifications that are within the scope of this invention.

What is claimed is:

1. An absorbent article comprising:
   (a) a topsheet having a body-facing surface and a core-facing surface;
   (b) a backsheet having a garment-facing surface and a core-facing surface;
   (c) an absorbent core disposed between the core-facing surface of the topsheet and the core-facing surface of the backsheet;
   (d) a printed article substrate having a first surface and a second surface opposing the first surface, the second surface of the printed article substrate being disposed on the garment-facing surface of the backsheet, the substrate being a non-woven web or a woven fabric; and
   (e) a composite image having a composite surface area, the composite image comprising a first artwork portion having a first surface area printed with an ink composition on the first surface of the substrate and a second artwork portion having a second surface area printed with an ink composition on either the second surface of the substrate or the garment-facing surface of the backsheet;
   wherein the first artwork portion comprises a first outline element,
   wherein the second artwork portion comprises a colored region,
   wherein the first and second artwork portions are vertically aligned such that the colored region of the second artwork portion is coincident with complementary regions of the outline element of the first artwork portion such that the first and second artwork portions are printed on the same position of the substrate and do not occupy different positions at any points in order to form the composite image;
   wherein the first artwork portion and the second artwork portion are visible when viewed from above the first surface.

2. The absorbent article of claim 1, wherein the second artwork portion is printed on the second surface.

3. The absorbent article of claim 1, wherein the printed article substrate is a synthetic non-woven web having a thickness of about 12 μm or more.

4. The absorbent article of claim 3, wherein the thickness is about 60 μm or more.

5. The printed article of claim 1, wherein the second artwork portion further comprises a second outline element.

6. The printed article of claim 1, wherein the ratio of the first surface area to the composite surface area is about 0.2 or less.

7. The printed article of claim 6, wherein the ratio is about 0.1 or less.

8. The printed article of claim 1, wherein the ratio of the sum of the first surface area and the second surface area to the composite surface area is in a range of greater than 1.0 to 2.0.

9. The printed article of claim 8, wherein the ratio is in a range of about 1.2 to 2.0.

10. The printed article of claim 3, wherein the thickness is about 400 μm or less.

11. The printed article of claim 3, wherein the thickness is in a range of about 80 μm to about 200 μm.

12. The absorbent article of claim 1, wherein the first surface of the printed article substrate includes a series of ridges and a series of recessions between the ridges.

13. The absorbent article of claim 1, wherein an ink composition is a water-based ink.

14. The absorbent article of claim 1, wherein an ink composition is a solvent based ink.

15. The absorbent article of claim 1, wherein an ink composition is a disappearing ink.

16. The absorbent article of claim 1, wherein the first artwork portion and the second artwork portion comprise the same ink composition.

17. The absorbent article of claim 1, wherein the first artwork portion and the second artwork portion comprise different ink compositions.

* * * * *